US011413238B2

(12) United States Patent
Domalaon et al.

(10) Patent No.: US 11,413,238 B2
(45) Date of Patent: Aug. 16, 2022

(54) N-ACETYLCYSTEINE COMPOSITIONS AND METHODS (71) Applicant: ENDO VENTURES LIMITED, Dublin (IE)

(72) Inventors: Ronald Domalaon, Raritan, NJ (US); Jinjiang Li, Monmouth Junction, NJ (US); Tushar Hingorani, Bridgewater, NJ (US); Kumaresh Soppimath, Skillman, NJ (US)

(73) Assignee: ENDO VENTURES LIMITED, Dublin (IE)

(*) Notice: Subject to any disclaimer, the term of this patent is extended or adjusted under 35 U.S.C. 154(b) by 0 days.

(21) Appl. No.: 17/177,797

(22) Filed: Feb. 17, 2021

(65) Prior Publication Data

US 2021/0251889 A1    Aug. 19, 2021

Related U.S. Application Data (60) Provisional application No. 62/978,128, filed on Feb. 18, 2020.

(51) Int. Cl.
| | |
|---|---|
| *A61K 9/00* | (2006.01) |
| *A61K 47/26* | (2006.01) |
| *A61K 47/02* | (2006.01) |
| *A61K 31/19* | (2006.01) |
| *A61J 1/10* | (2006.01) |

(52) U.S. Cl.
CPC ............ *A61K 9/0019* (2013.01); *A61K 31/19* (2013.01); *A61K 47/02* (2013.01); *A61K 47/26* (2013.01); *A61J 1/10* (2013.01)

(58) Field of Classification Search
CPC ...... A61K 9/0019; A61K 31/19; A61K 47/02; A61K 47/26; A61J 1/10
See application file for complete search history.

(56) References Cited

U.S. PATENT DOCUMENTS

| | | | |
|---|---|---|---|
| 6,391,332 B1 * | 5/2002 | Somerville | ............ A23L 33/10 424/439 |
| 2007/0049640 A1 | 3/2007 | Pavliv | |
| 2011/0014285 A1 | 1/2011 | Herzenberg et al. | |
| 2012/0022161 A1 * | 1/2012 | Pavliv | .................. A61K 31/197 514/562 |
| 2018/0055801 A1 | 3/2018 | Pavliv | |

FOREIGN PATENT DOCUMENTS

| | | |
|---|---|---|
| CN | 101028252 A | 9/2007 |
| CN | 101239037 A | 8/2008 |
| WO | 2007024311 A1 | 3/2007 |

OTHER PUBLICATIONS

ACETADOTE Package Insert, Cumberland Pharmaceuticals Inc., Nashville, TN, Jun. 2013; 8 pgs.

* cited by examiner

*Primary Examiner* — Robert A Wax
*Assistant Examiner* — Quanglong N Truong
(74) *Attorney, Agent, or Firm* — ArentFox Schiff LLP (57) ABSTRACT

Storage stable sterile ready-to-administer formulations comprising N-acetylcysteine are presented with desirable stability characteristics. In preferred aspects, formulations comprise low quantities of one or more chelating agents, contain N-acetylcysteine at a concentration of 25 mg/mL or 50 mg/mL, and are packaged in a suitable format, such as a polymeric bag with a metalized overwrap and a non-contact oxygen scavenger.

12 Claims, 1 Drawing Sheet

N-ACETYLCYSTEINE COMPOSITIONS AND METHODS

This application claims priority to our U.S. Provisional Patent Application with the Ser. No. 62/978,128, which was filed Feb. 18, 2020, and which is incorporated by reference herein.

FIELD OF THE INVENTION

The present disclosure relates to pharmaceutical compositions and methods, especially as they relate to storage stable and ready-to-administer formulations of N-acetylcysteine.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Figure 1:
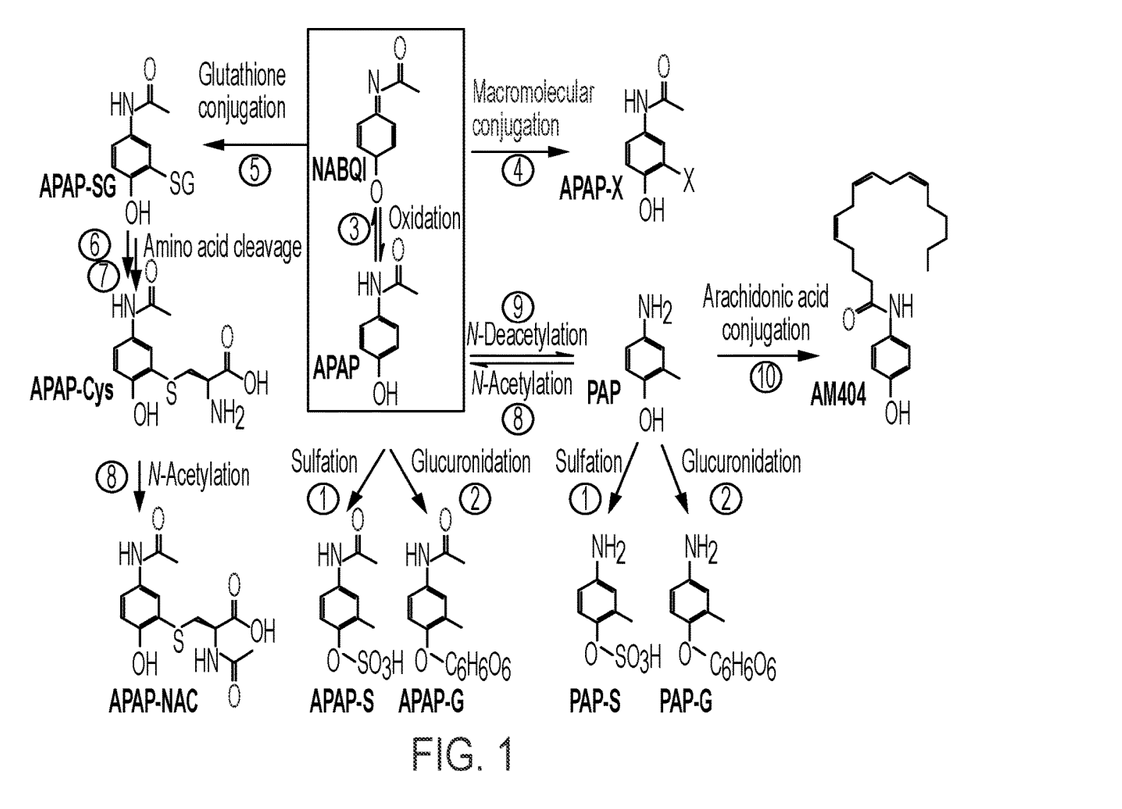
FIG. 1 schematically depicts exemplary degradation pathways for acetaminophen.

Acetaminophen, commonly known as paracetamol, is a household analgesic medication used to alleviate pain and fever. Acetaminophen is transformed in the liver to sulfate and glucuronide conjugates as forms of non-toxic metabolites that are then excreted in urine. However, a small portion of acetaminophen is also oxidatively transformed by isozyme CYP2E1 of the cytochrome P450 mixed function oxidase enzyme system in the liver to yield a reactive, and potentially toxic, intermediate called N-acetyl-p-benzoquinoneimine (NAPQI) as is schematically shown in FIG. 1. This highly oxidative metabolite is a strong electrophile and is detoxified by glutathione (reduced form). Upon acetaminophen overdose, normal hepatic metabolism via sulfate and glucuronide cascades is overloaded, resulting in elevated NAPQI levels, which then deplete cellular glutathione storages. Consequently, excess NAPQI interacts with a variety of cellular components, and especially enzymes resulting in the disruption of function and overall cell death. Overdose by ingestion of 10-15 g of acetaminophen in a single dose was reported to result in hepatic damage after 2-5 days with significant morbidity resulting from complete hepatic failure.

Most commonly, acetylcysteine is administered intravenously for the treatment of acetaminophen overdose. It is most effective in preventing hepatic toxicity if administered within 8-10 hours post acetaminophen overdose. Acetylcysteine protects the liver by promoting glutathione synthesis to replenish cellular stores. Deacetylation of acetylcysteine in the body yields L-cysteine that is consequently used to construct cellular glutathione. Moreover, acetylcysteine and L-cysteine can act as an alternative substrate to glutathione in detoxifying NAPQI. The D-isomer of acetylcysteine has been reported to not prevent hepatotoxicity unlike the L-isomer.

A half-life ($T_{1/2}$) of 5.7 hours was reported following an intravenous administration of acetylcysteine. It has a complicated metabolic profile as it is transformed into several products (such as cysteine, cystine, methionine, glutathione, mixed disulfides, etc.) in the body. However, 20-30% of administered acetylcysteine was reported to be excreted in the urine unchanged. Potential adverse reactions following intravenous administration of acetylcysteine include acute flushing and erythema of the skin, and anaphylactoid reactions (now termed as nonimmunologic anaphylaxis) such as rash, urticaria, pruritis, hypotension, wheezing and/or shortness of breath.

Acetylcysteine, also known as N-acetyl-L-cysteine or N-acetylcysteine, is the acetyl derivative of the naturally occurring amino acid L-cysteine. Acetylcysteine is used in the treatment of acetaminophen-overdose-induced hepatotoxicity. Acetylation of the N-terminus render the reactive amine into a relatively less reactive amide. Acetylcysteine is a chiral molecule with the L-isomer being active while the D-isomer is inactive. Acetylcysteine exists as a white crystalline powder that has a melting point range of 109-110° C. and exudes a very slight acetic odor. Acetylcysteine is non-hygroscopic and is stable in ambient light.

N-acetylcysteine

Acetylcysteine is an antioxidant in biological systems and is a precursor of the tripeptide glutathione that is responsible for neutralizing oxidative elements such as free radicals in humans and animals. Acetylcysteine is deacetylated in biological systems (e.g., blood, gut, etc.) to generate L-cysteine and therefore is considered a prodrug.

Solubility of acetylcysteine has been reported to be 1 gram in 5 mL water or 4 mL alcohol. However, it is insoluble in chloroform and ether. It has three rotatable bonds, three hydrogen bond donors and three hydrogen bond acceptors. Acetylcysteine has an octanol/water partition coefficient (LogP) of -0.66 (estimated), reflecting its highly polar nature. Acetylcysteine does not react with glass, plastic, aluminum, anodized aluminum, chromed metal and stainless steel, however, solutions of acetylcysteine react upon contact with rubber, some metals (particularly iron and copper surfaces), and/or when subjected to autoclaving, leading to discoloration and hydrogen sulfide generation.

Chemical stability issues, and particularly oxidative degradation in aqueous solutions of acetylcysteine are well known in the art, and various attempts have been made to solve problems associated with hydrolysis, nucleophilic attack, and oxidation. For example, acetylcysteine is stabilized in solution by inclusion of tromethamine as is described in CN 101239037. However, tromethamine may not be desirable in all uses of acetylcysteine. In further known methods, WO 2007/024311 describes preparation of a concentrated solution of acetylcysteine where oxygen depleted solvent at pH 6.8 provided unexpected chemical stability of the solution. However, such solution is a concentrate and requires appropriate dilution prior to use. In yet other known methods, acetylcysteine is provided as a lyophilized powder along with a buffer agent as described in CN 101028252. Once more, reconstitution is required prior to administration, which adds delay to treatment and introduces potential errors. Similarly, various concentrated acetylcysteine solutions are known in the art (e.g., ACETADOTE, 200 mg/mL acetylcysteine concentrate by Cumberland Pharmaceuticals Inc.), which once more require dilution.

Regardless of the particular formulation, concentrated acetylcysteine solutions present a further potential hazard as such concentrated solutions require significant calculations to determine the appropriate dilution factor and volume for a given administration. In particular, acetylcysteine administration is not only dependent on the body weight of the subject receiving the medication, but also administered in three distinct dosages: a higher loading dose (150 mg/kg), a lower second dose (50 mg/kg), and an intermediate third dose (100 mg/kg). As such, multiple administrations at different dosages introduce multiple points of potential contamination and dosing errors.

Thus, even though various acetylcysteine formulations are known in the art, all or almost all of them suffer from various disadvantages. Consequently, there is a need to provide improved compositions and methods that provide storage stable and ready-to-administer formulations of N-acetylcysteine that can reduce the risk of potential contamination and dosing errors.

SUMMARY OF THE INVENTION

Compositions and methods are presented that provide desirable stability for aqueous solutions of N-acetylcysteine, and especially for ready-to-administer injectable formulations. Moreover, contemplated compositions will advantageously have a fixed concentration for use and will so avoid potential risks due to contamination and/or miscalculation for dilution. For example, contemplated formulations will comprise N-acetylcysteine at a fixed concentrations of about 25 mg/mL or 50 mg/mL and have a pH in the range of about pH 6.0-7.5 (e.g., pH 7.0), preferably in the presence of one or more metal chelators at low concentrations such as 10-60 mcg/mL.

In one aspect of the inventive subject matter, the inventors contemplate a method of administering N-acetylcysteine to a subject in need thereof that includes a step of providing a sterile and ready-to-administer composition comprising N-acetylcysteine containing N-acetylcysteine at a fixed concentration, and a further step of administering, without prior dilution, the ready-to-administer composition to a subject in need thereof in three distinct doses, wherein the fixed concentration of the N-acetylcysteine is the same in each of the three doses. Most typically, the ready-to-administer composition comprises a metal chelator (e.g., ethylenediamine tetraacetic acid, preferably at a concentration of between 10 and 60 mcg/mL) and has a pH between 6.0 and 7.5, and optionally further includes an antioxidant and/or a tonicity agent (typically NaCl). The ready-to-administer composition presented herein preferably contains, after storage over at least three weeks at 80° C., equal or less than 7%, equal or less than 6%, or equal or less than 5% total impurities generated from degradation of the N-acetylcysteine.

In some embodiments, the fixed concentration is 25 mg/mL or 50 mg/mL, and/or the ready-to-administer composition has a pH of 7.0±0.2. It is further contemplated that administration of a first dose and at least part of a second dose of the three doses may be done from a single container containing the ready-to-administer composition. Alternatively, administration of each of the three doses may also be done from respective separate containers, each containing the ready-to-administer composition. Therefore, suitable containers may have a volume of between 50 and 500 mL (e.g., between 200 and 300 mL). It is still further contemplated that the composition is filter sterilized or autoclaved.

In further embodiments, a first of the three doses is administered over 1 hour, wherein a second of the three doses is administered over 4 hours, and wherein a third of the three doses is administered over 16 hours. Where desired, the administering the ready-to-administer composition is performed using an infusion pump.

Therefore, the inventors also contemplate a sterile and ready-to-administer N-acetylcysteine composition that includes an aqueous solution containing N-acetylcysteine at a concentration suitable for direct administration via intravenous injection to a patient without dilution prior to administration. Most typically, such composition has a pH of between 6.0 and 7.5 and comprises a chelating agent at a concentration of between 10 and 60 mcg/mL. As noted before, it is contemplated that the ready-to-administer composition contains, after storage over at least three weeks at 80° C., equal or less than 7% or 6% or 5% total impurities generated from degradation of the N-acetylcysteine. In preferred compositions the N-acetylcysteine concentration is 25 mg/mL or 50 mg/mL, and the composition has a pH of 7.0±0.2.

Viewed from another perspective, the inventors also contemplate a kit that includes a primary container that contains a sterile and ready-to-administer N-acetylcysteine composition as presented herein, a secondary container enclosing the primary container, and a non-contact oxygen absorbing agent in a space between the primary and secondary container. Most typically, the primary container contains between 100 and 500 mL of the ready-to-administer N-acetylcysteine composition, and the secondary container is a polymeric container that may or may not be impermeable to light or comprise a metal or metal layer.

In preferred aspects, the primary container contains 50 mL or 100 mL or 150 mL or 200 mL or 250 mL or 300 mL or 350 mL or 400 mL or 450 mL or 500 mL of the ready-to-administer N-acetylcysteine composition, and/or the primary and secondary containers are polymeric bags. It is further generally preferred that the ready-to-administer N-acetylcysteine composition is preservative-free.

Various objects, features, aspects, and advantages will become more apparent from the following detailed description of preferred embodiments, along with the accompanying drawing in which like numerals represent like components.

DETAILED DESCRIPTION

The inventors have now discovered that sterile storage stable, aqueous, and ready-to-administer N-acetylcysteine formulations can be prepared that not only have a desirable stability profile but that also have a fixed concentration suitable for immediate administration to a subject without need for prior dilution. Therefore, even complex modes of administration as discussed below can be performed in a very simple manner that will entirely avoid potential risks associated with dilution mistakes and microbial contamination.

Most preferably, contemplated compositions will contain acetylcysteine at a fixed concentration 25 mg/mL or 50 mg/ml and are packaged into suitable containers such as IV bags at a volume of 200 ml or 300 ml bag for an acetylcysteine concentration of 50 mg/ml or at a volume of 250 ml bag at an acetylcysteine concentration of 25 mg/ml. It should be appreciated that such presentation will not only avoid issues with on-site dilution, dilution errors, points of contamination, etc., but also avoids osmolality/tonicity issues arising from different dilution factors needed for a concentrate (e.g., 200 mg/mL) to achieve a specific dosage regimen as is also discussed in more detail below. Viewed from a different perspective, contemplated compositions also eliminate help reduce significant fluid loads to a subject. Still further, it should be appreciated that administration of specific dosages of the compositions presented herein can be controlled via administered volume over time from a single container. Therefore, residual quantities of the composition can be 'carried over', for example, from a loading dose to a maintenance ($2^{nd}$) dose, or from a $2^{nd}$ dose to a $3^{rd}$ dose. Thus, and contrary to conventional practice, administration of a specific dose is not achieved by depletion of a fluid container that was prefilled with a specific dose, but by typically metered delivery of a predetermined volume (e.g., via control of the drip rate for predetermined time/volume). Moreover, the formulations presented herein can be aseptically filled or terminally sterilized and packaged in a format that maintains protection from oxygen ingress.

More specifically, and as is shown in more detail below, the inventors discovered that formulations can be prepared that will contain after storage over at least three weeks less than 8%, or less than 7%, or less than 6%, or less than 5%, or less than 4%, or less than 3% of total impurities from the degradation of N-acetylcysteine as determined by HPLC-UV at 25° C. or even at accelerated storage conditions such as storage at 40° C., or 60° C., or even 80° C. Notably, such stability at low concentrations is particularly remarkable as these formulations will typically contain very low concentrations of chelators, preferably less than 100 mcg/mL, or equal or less than 60 mcg/mL, or equal or less than 50 mcg/mL, or equal or less than 40 mcg/mL, or equal or less than 30 mcg/mL, or equal or less than 20 mcg/mL, or equal or less than 10 mcg/mL. Thus, it is expected that the formulations presented herein will have excellent storage stability of at least 1 month, or at least 2 months, or at least 3 months, or at least 6 months, or at least 9 months, or at least 12 months, or at least 18 months, or at least 24 months, even at elevated storage temperatures (e.g., accelerated storage conditions such as 40° C., or 60° C., or even 80° C.). Moreover, such formulations are also contemplated to be subjected to thermal sterilization, and particularly autoclaving to sterility (e.g., over at least 5 min, or at least 10 min, or at least 15 min at 121° C.), without substantial increase in degradation.

Such stability is particularly remarkable in view of the diverse pathways through which N-acetylcysteine can degrade. As is described in more detail below, N-acetylcysteine can degrade though oxidation, hydrolysis, and nucleophilic reactions due to the presence of various reactive functional moieties in N-acetylcysteine. For example, N-acetylcysteine can be subject to cyclization reactions under acidic and basic conditions to form 5-membered ring degradation products as is discussed in more detail below.

As noted above, acetylcysteine has various functional moieties that render the molecule susceptible to degradation under aqueous conditions. More specifically, acetylcysteine is very labile at extreme pHs and can undergo hydrolysis and nucleophilic reactions at highly acidic and basic pHs. Among other reactions, nucleophilic reactions can include intramolecular cyclization and intermolecular reactions with excipients. Acetylcysteine is also highly susceptible to oxidizing agents such as reactive oxygen species and free radicals. Therefore, it should be appreciated that several degradative routes for acetylcysteine exist.

Hydrolysis: The amide bond in acetylcysteine imparts chemical lability in the presence of nucleophiles at promoting conditions such as highly acidic and basic pHs. Water, existing as predominantly hydroxyl or hydronium ions depending on the pH, can promote the hydrolysis of amide bond that resulting in the degradation of acetylcysteine to L-cysteine and acetic acid. The amide bond of amino acid-containing molecules such as peptides and N-acetylated amino acids at neutral pH in the absence of a catalyst (to lower bond breaking activation energy) is perceived to be robust. For instance, glycyl-D-valine amide/peptide bond was estimated to have a half-life of 267 years at pH 7 and 37° C. However, the rate of hydrolysis significantly increases once the pH moves towards the extremes (pH<5 and >9). Therefore, the inventors contemplate that a pH between the range of 5-9 may be suitable for a formulation of acetylcysteine to minimize, if not prevent hydrolysis of the acetyl amide bond.

Figure 2:
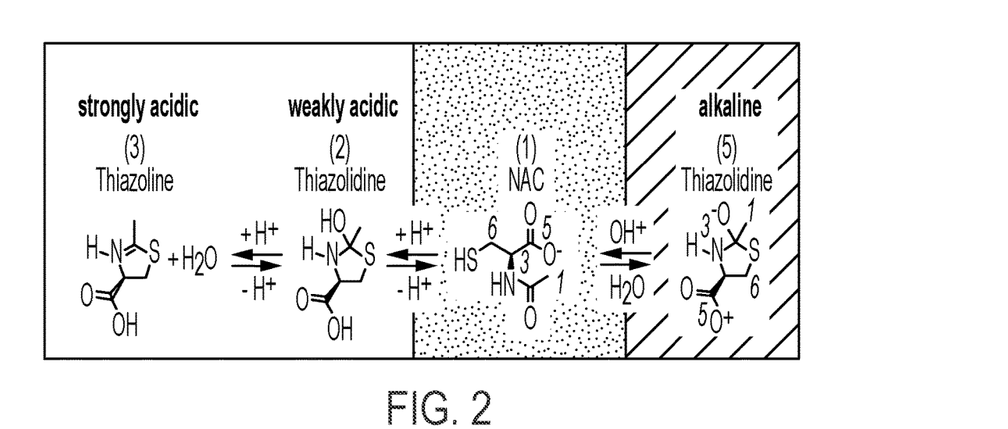
FIG. 2 schematically depicts exemplary cyclization reactions of N-acetylcysteine at highly acidic conditions to form a thiazoline degradation product and at highly basic conditions to for, a thiazolidine degradation product.

Nucleophilic reaction: It has been very well documented that the electron-rich thiol sidechain of Acetylcysteine act as a nucleophile at extreme pHs. At highly acidic pH, the carbonyl oxygen of the amide can abstract a proton in solution to exist as an activated cationic form. Intramolecular cyclization is initiated by nucleophilic attack of thiol's sulfur atom resulting to a five-membered thiazolidine ring as is schematically shown in FIG. 2. Subsequently, water is expelled to generate a five-membered thiazoline ring in highly acidic solutions. While thiol sulfur can theoretically carry out a nucleophilic attack at the carbonyl carbon of the carboxylic acid C-terminus (post protonation of the carbonyl oxygen at highly acidic pH to yield an activated cationic form), cyclization resulting to four-membered rings are thermodynamically and kinetically unfavorable. Four-membered rings are inherently unstable due to bond constrains and therefore are not expected to form under normal conditions. Conversely, the thiol group can be deprotonated at highly basic conditions promoting its nucleophilic attack to the carbonyl carbon of the amide. This intramolecular reaction yields a five-membered thiazolidine ring as is schematically shown in FIG. 2. In contrast to acidic media, loss of water cannot occur for a thiazolidine ring since basic condition promotes and stabilize the resulting anion, and that the generation of a good leaving group is prevented.

Intermolecular nucleophilic attack of acetylcysteine's thiol group also occurs at both acidic and basic pH. For instance, the thiol sulfur of a molecule can perform a nucleophilic attack on an activated carbonyl carbon of another molecule resulting to a dipeptide derivative. The thiol group can also react with excipients having electrophilic moieties. These can be particularly problematic under thermal conditions since heat enhance the kinetics of reaction (introduced thermal energy increases movements of particles and therefore their collision/reaction with one another). Therefore, the inventors contemplate that acetylcysteine should be maintained at neutral pH (5-9) to prevent intramolecular cyclization reactions. Consequently, excipients with labile electrophilic moieties such as reducing sugars are preferably limited, if not entirely avoided in contemplated formulations.

Oxidation (redox reaction): Acetylcysteine readily loses electrons by one-electron or two-electron oxidation processes and reduce oxidizing agents such as free radicals. Depending on the oxidizing agent, different oxidation products and adducts are produced including disulfides such as cystine. Specifically, cystine is produced when the thiol group of two L-cysteine (deacetylated acetylcysteine) lose electrons and react with one another forming a disulfide bond. Rate constants for the reaction of acetylcysteine with various free radicals and reactive compounds are known and exemplary data are shown in Table 1. Acetylcysteine is very labile in the presence of hydroxyl and nitrogen dioxide radicals. Hydroxyl radicals are typically generated in solution from peroxides such as hydrogen peroxide ($H_2O_2$) via divalent iron cation ($Fe^{2+}$)-catalyzed Fenton reaction with molecular oxygen ($O_2$). Interestingly, Acetylcysteine is not reactive towards hydrogen peroxide as indicated by the rate constant of $0.85 \pm 0.09$ $M^{-1}s^{-1}$. It has also been suggested that molecular oxygen do not directly oxidize acetylcysteine. However, molecular oxygen indirectly affects the stability of acetylcysteine as it participates in the formation of reactive oxygen species such as a hydroxyl radical and superoxide anion. Formation of such free radicals and reactive oxygen species are promoted in the presence of molecular oxygen and can be catalyzed by metal cations, thermal activation, and irradiation. The inventors therefore concluded that the dissolved oxygen content should be minimized and that any metal cations in the formulation should be sequestered. It should be noted that acetylcysteine can also chelate metal cations as described in more detail below. In view of these considerations, the inventors particularly contemplate use of a metal chelator excipient that has a higher metal complex formation constant (log K) for anticipated metal cations in the formulation as compared to the metal complex formation constant of acetylcysteine.

TABLE 1

| Reactive compound | Rate constant ($M^{-1}$ $s^{-1}$) | Experimental Conditions |
| --- | --- | --- |
| Hydroxyl radical (•OH) | $1.36 \times 10^{10}$ | pH 7, RT |
| Superoxide anion ($O_2^{•-}$) | $68 \pm 6$ | pH 7, RT |
| Hydrogen peroxide ($H_2O_2$) | $0.85 \pm 0.09$ | pH 7.4, 25° C. |
| Peroxynitrite | $415 \pm 10$ | pH 7.4, 37° C. |
| Nitrogen dioxide radical (•$NO_2$) | $\sim 1.0 \times 10^7$ | pH 7.4, RT |
| Nitroxyl (HNO) | $5 \times 10^5$ | pH 7.4, 37° C. |
| NAPQI | $(1.36 \pm 0.2) \times 10^4$ | pH 7, 25° C. |

Peroxynitrite has been reported to react with acetylcysteine (at a rate constant of $415\pm10$ $M^{-1}s^{-1}$). It should be noted that peroxynitrite readily decomposes in solution to generate hydroxyl and nitrogen dioxide radicals and therefore much lability of acetylcysteine is due to peroxynitrite's degradants. Acetylcysteine is also reactive towards nitroxyl (HNO) which is the reduced and protonated form of nitric oxide. These reactive nitrogen species can be present in nitrite-containing excipients and/or from degradation thereof. Therefore, the inventors also contemplate that nitrites and nitrates should be avoided as excipients or trace impurities.

Based on the above considerations, the inventors also investigated additional parameters, including redox potential, and metal chelation and exemplary considerations are as follows.

Redox Potential: Acetylcysteine was described to have a redox potential of +63 mV relative to Glutathione (reduced GSH/oxidized GSSG) system as a reference standard. Thiol-containing molecules such as acetylcysteine, glutathione and L-cysteine are known to neutralize/reduce free radicals (oxidizing agents) by donating electrons from its electron-rich sulfur atom. Glutathione was described to be highly reducing at physiological conditions and have an experimental redox potential of −289 mV in the cytosol and therefore to an extent so does Acetylcysteine. Therefore, the inventors contemplate that it may be beneficial to omit the use of highly oxidizing agents in acetylcysteine formulations. Furthermore, the inventors contemplate that formation and dissemination of free radicals in solution should be prevented to avoid oxidation of acetylcysteine.

Metal chelation: Acetylcysteine possess metal chelation capabilities due to its thiol and carboxylic functional groups. Metal complex formation/stability constants (log K) for acetylcysteine at aqueous solutions are shown in Table 2. Ethylenediaminetetraacetic acid (EDTA), also known as edetic acid, and diethylenetriaminepentaacetic acid (DTPA), also known as pentetic acid, are shown for comparison since the two are considered the 'gold standard' metal chelators. The ability to chelate metal cations of acetylcysteine is greatly subpar in comparison to EDTA and DTPA.

TABLE 2

| | Complex formation constant (log K) | | | |
|---|---|---|---|---|
| Metal cation | EDTA | DTPA | Acetylcysteine | Experimental conditions for Acetylcysteine |
| $Fe^{3+}$ | 25.10 | 28.60 | 10.58 | 25° C. and 0.12 mol · $dm^{-3}$ ionic strength ($NaClO_4$) |
| $Cu^{2+}$ | 18.80 | 21.53 | 9.02 | 25° C. and 0.1 mol · $dm^{-3}$ ionic strength ($KNO_3$) |
| | | | 6.64 | 37° C. and 0.15 mol · $dm^{-3}$ ionic strength (NaCl) |
| $Ni^{2+}$ | 18.62 | 20.32 | 5.02 | 25° C. and 0.12 mol · $dm^{-3}$ ionic strength ($NaClO_4$) |
| | | | 4.86 | 37° C. and 0.15 mol · $dm^{-3}$ ionic strength (NaCl) |
| $Zn^{2+}$ | 16.50 | 18.75 | 7.04 | 25° C. and 0.1 mol · $dm^{-3}$ ionic strength ($KNO_3$) |
| | | | 6.23 | 37° C. and 0.15 mol · $dm^{-3}$ ionic strength (NaCl) |
| $Co^{2+}$ | 16.31 | 18.40 | 4.18 | 25° C. and 0.12 mol · $dm^{-3}$ ionic strength ($NaClO_4$) |
| | | | 4.28 | 37° C. and 0.15 mol · $dm^{-3}$ ionic strength (NaCl) |
| $Cr^{3+}$ | 23.40 | — | 8.26 | 25° C. and 0.12 mol · $dm^{-3}$ ionic strength ($NaClO_4$) |
| $Cd^{2+}$ | 16.46 | 19.31 | 7.25 | 25° C. and 0.1 mol · $dm^{-3}$ ionic strength ($KNO_3$) |
| $Hg^{2+}$ | 21.80 | 27.00 | 11.23 | 25° C. and 0.1 mol · $dm^{-3}$ ionic strength ($KNO_3$) |
| $Mn^{2+}$ | 14.04 | 15.60 | 3.64 | 37° C. and 0.15 mol · $dm^{-3}$ ionic strength (NaCl) |

Metal complexation in the presence of molecular oxygen promotes oxidation of acetylcysteine in aqueous solutions. As already noted above, the inventors therefore contemplate that it might be beneficial to include excipients with stronger chelation potency than acetylcysteine, such as EDTA and DTPA, in the formulation to competitively sequester metal cations. Both EDTA and DTPA are expected to have stronger metal complex equilibrium (would likely retain the metal bounded) to mask the metal from reacting with molecular oxygen and other radical promoting species.

Based on the above and further considerations, the inventors therefore contemplate that aqueous formulations with ready-to-administer acetylcysteine concentrations will generally fall within a relatively narrow range of pH and will further avoid a variety of components otherwise commonly used in pharmaceutical formulations. Moreover, contemplated formulations will preferably contain one or more chelating agents at relatively low concentrations, which will also not interfere with chemical stability of acetylcysteine.

For example, an exemplary formulation according to the inventive subject matter will include acetylcysteine at a concentration of 25 mg/mL or 50 mg/mL and will further include EDTA as a chelator at a concentration of between 10 and 60 mcg/mL. Most typically, such formulations are prepared using water for injection and the pH will be adjusted with NaOH to pH 7.0. Advantageously, such formulations will not require any antioxidant and buffer.

With respect to contemplated acetylcysteine concentrations it is typically preferred that the acetylcysteine is present in the formulation at a final concentration of at least 1 mg/mL, or at least 5 mg/mL, or at least 10 mg/mL, or at least 25 mg/mL, or at least 50 mg/mL, or at least 75 mg/mL, or at least 100 mg/mL, or even higher. Therefore, suitable concentration ranges for acetylcysteine in the final formulation will be between 1 and 10 mg/mL, or between 10 and 40 mg/mL, or between 25 and 75 mg/mL, or between 50 and 100 mg/mL, or even higher. Viewed from a different perspective, suitable acetylcysteine concentrations will be 10 mg/mL, or 25 mg/mL, or 50 mg/mL, or 75 mg/mL, or 100 mg/mL, and even higher. Thus, it should be recognized that the acetylcysteine in the final formulation will have a concentration that is suitable for injection without further need for dilution. It should be noted that these and all other concentrations mentioned herein may also be approximate concentrations that have a variability of ±5%, or ±10%, or ±15%, or ±20% of the given value.

As already noted above, the acetylcysteine concentrations contemplated herein will generally have an acidic pH which will generally be equal or less than 7.5, or equal or less than 7.0, or equal or less than 6.5, or equal or less than 6.0, or equal or less than 5.5, and in some cases even less. Thus, contemplated pH ranges will typically be between 5.5 and 6.5, or between 6.0 and 7.0, or between 6.5 and 7.5. For example, contemplated formulations may have a pH of 5.5±0.2, or may have a pH of 5.8±0.2, or may have a pH of 6.0±0.2, or may have a pH of 6.3±0.2, or may have a pH of 6.5±0.2, or may have a pH of 6.8±0.2, or may have a pH of 7.0±0.2, or may have a pH of 7.2±0.2.

While it is generally preferred that contemplated formulations will be adjusted to a desirable pH without use of a buffer, various buffers and buffer systems including organic, inorganic, and amphoteric buffers are nevertheless deemed suitable for use herein. Therefore, especially contemplated buffer systems include phosphate buffers MOPS, HEPES, MES, Bis-TRIS, etc. Most typically, and while not limiting to the inventive subject matter, the inventors contemplate that the buffer strength required for stabilization of acetylcysteine will be relatively low, for example, equal or less than 100 mM, and more typically equal or less than 50 mM, and most typically between 5 mM and 20 mM (e.g., 10 mM). Therefore, contemplated buffers will generally have a concentration of between about 0.1-1 mM, or between about 1-5 mM, or between about 5-10 mM, or between about 10-20 mM, or between about 2-50 mM, and in some cases higher.

In still further contemplated aspects, the formulations presented herein will also include one or more chelating agents, and particularly metal ion chelators. For example, suitable chelators include various bicarboxylic acids, tricarboxylic acids, and aminopolycarboxylic acids such as ethylenediaminetetraacetic acid (EDTA), ethylene glycol-bis ((3-aminoethyl ether)-N,N,N',N'-tetraacetic acid (EGTA), and penta(carboxymethyl)diethylenetriamine (DTPA), and salts and hydrates thereof. While not limiting to the inventive subject matter, it is contemplated that the metal ion chelators will slow down both the baseline and metal ion-stimulated degradation of acetylcysteine. Remarkably, the inventors unexpectedly observed that the desirable effect of the chelators was observable at relatively low concentrations of the chelators. For example, reduction of the baseline and metal ion-stimulated degradation of acetylcysteine was observed at chelator concentrations of between 1 mcg/ml and 10 mcg/ml, between 10 mcg/ml and 30 mcg/ml, between 30 mcg/ml and 50 mcg/ml, between 50 mcg/ml and 70 mcg/ml, or between 70 mcg/ml and 100 mcg/ml. Interestingly, the chelators, and especially the aminopolycarboxylic acids retained stabilizing effect despite the relatively low pH favoring protonated forms of the chelators. In further embodiments, the chelator may also be omitted, especially where compounding will avoid use of metal containers.

In yet further preferred aspects, it should be appreciated that contemplated formulations will not require an antioxidant. However, it should be noted that one or more antioxidants could be included, and particularly preferred antioxidants include cysteine hydrochloride, methionine, ascorbic acid, tocopherol, and sodium metabisulfite. Most antioxidants are deemed to have stabilizing effect even when used at relatively low concentrations, and preferred concentrations include those between 0.1-5 mcg/mL, or between 5-10 mcg/mL, or between 10-30 mcg/mL, or between 30-50 mcg/mL, or between 50-100 mcg/mL. Thus, contemplated antioxidant concentrations may be 1 mcg/mL, or 5 mcg/mL, or 10 mcg/mL, or 25 mcg/mL, or 50 mcg/mL, or 100 mcg/mL.

With respect tonicity agents, it is generally contemplated that all known tonicity agents can be used in conjunction with the teachings presented herein and suitable tonicity agents include various carbohydrates (e.g., dextrose, mannitol, etc.), glycols (e.g., glycerol), and pharmaceutically acceptable salts (e.g., NaCl). The amount of tonicity adjusting agent used can be adjusted to obtain an osmolality of the formulations in the range of 260 to 340 mOsm/kg. An osmometer can be used to check and determine or adjust the amount of tonicity adjusting agent to be added to obtain the desired osmolality.

Notably, contemplated acetylcysteine formulations were stable as described in more detail below, especially where deoxygenated solvents (e.g., typically water and/or buffer) were employed. Deoxygenation (i.e., reduction of molecular dissolved oxygen) can be achieved in numerous manners, including sparging with inert gases (e.g., helium, various freons, argon, xenon), agitation under vacuum, and/or using enzymatic systems that deplete a solution of dissolved oxygen (see e.g., U.S. Pat. No. 9,187,779). Moreover, it is generally preferred that any headspace in the container will be maintained under an oxygen-reduced or depleted state. Additionally, or alternatively, ingress of molecular oxygen into the formulation can also be reduced by co-packaging a container with the formulation in a secondary container that includes an oxygen scavenger, and especially a metal-free oxygen scavenger (e.g., GLS100, Ageless®, Pharmakeep®, all commercially available from Mitsubishi Gas Chemical America). Therefore, it should be noted that non-contact oxygen scavengers are especially preferred.

With respect to the sterilization of contemplated formulations it should be appreciated that contemplated formulations may be sterilized using all known manners of sterilization, including filtration through 0.22 micron filters, heat sterilization, autoclaving, radiation (e.g., gamma, electron beam, microwave), and gas sterilization (e.g., using ethylene oxide gas). Based on the anticipated moderate stability, the formulations contemplated herein are filtered through a 0.22-micron (or other suitably sized) filter, and then filled in to a container such as a polyethylene, polypropylene, or low-density polyethylene container. Where desired, the filling may include a blow-fill-seal (BFS) process.

BFS is a form of advanced aseptic manufacturing wherein the container is formed, filled, and sealed in one continuous, automated system not requiring human intervention. The process begins with the extrusion of plastic granules in the form of a hot hollow pipe of molten plastic called a parison. The next step is the blow molding of the container with an open top through which the container is filled, all while the plastic remains hot and in a molten state. Once filled, the container is hermetically sealed and cooled. The blow-fill seal process can take several seconds, and contemplated ready-to-inject compositions advantageously are formulated to withstand the temperature and pressure requirements without substantial degradation of acetylcysteine (e.g., less than 5 wt %, less than 3 wt %, less than 2 wt %, less than 1 wt % degradation).

Once the acetylcysteine formulations are filled in large volume polymeric, semi-permeable infusion containers (e.g., BFS container or flexible IV bags), the containers can optionally be layered or covered with a secondary packaging system optionally including an oxygen scavenger. For example, the BFS containers can further be sealed in an oxygen and moisture barrier blister packaging. The blister packaging can comprise one or more layers, and the one or more layers can include aluminum foil or other oxygen absorber having an Oxygen Transmission Rate (OTR) between 0.0005 to 5.00 cc/100 in$^2$/24 hrs. Additionally or alternatively, one or more oxygen absorbers (metal or metal free, organic material) can be incorporated into any portion of the BFS container, the secondary packaging system, or between the two (e.g., between the BFS container and the multi-layer packaging) such that the oxygen absorber removes at least a portion of oxygen from the air surrounding said oxygen-sensitive drug. A beneficial feature of the oxygen absorber is the absorbance and removal of oxygen present in the primary packaging and in the liquid drug itself. Notably, it was found that the oxygen absorber also removed residual headspace oxygen in the primary packaging and also dissolved oxygen in the liquid over time, thereby further improving stability of acetylcysteine. In still further contemplated but less preferred aspects, the container may also be a glass container.

As is described in more detail below, contemplated compositions exhibit significant storage stability over extended periods of time, even where the storage is at ambient (25° C.) or significantly higher temperatures such as 40° C., or 60° C., or even 80° C. In most cases, stability can be expressed as the presence of total impurities where the impurities are generated from the degradation of the acetylcysteine via one or more degradation pathways. For example, contemplated composition will typically have a storage stability at ambient temperature (25° C.) of at least 6 months, or at least 12 months, or at least 18 months, or at least 24 months, after which equal or less than 10%, or equal or less than 8%, or equal or less than 7%, or equal or less than 6%, or equal or less than 5%, or equal or less than 4%, or equal or less than 3% of total impurities are present are generated from the degradation of the acetylcysteine. Similarly, it is contemplated that contemplated composition will typically have a storage stability at elevated storage temperature (40 or 60° C.) of at least 3 months, or at least 6 months, or at least 12 months, or at least 18 months, after which equal or less than 10%, or equal or less than 8%, or equal or less than 7%, or equal or less than 6%, or equal or less than 5%, or equal or less than 4%, or equal or less than 3% of total impurities are present are generated from the degradation of the acetylcysteine. Likewise, it is contemplated that contemplated composition will typically have a storage stability at high ultra-high storage temperature (80° C.) of at least 2 weeks, or at least 3 weeks, or at least 4 weeks, or at least 6 weeks, or at least 12 weeks, after which equal or less than 10%, or equal or less than 8%, or equal or less than 7%, or equal or less than 6%, or equal or less than 5%, or equal or less than 4%, or equal or less than 3% of total impurities are present are generated from the degradation of the acetylcysteine. Of course, it should be appreciated that the compositions presented herein will exceed under refrigeration (4-8° C.) the stability otherwise observed for storage 12 months, or at least 18 months, or at least 24 months at ambient temperature.

In yet further contemplated aspects, the acetylcysteine compositions presented herein are preferably packaged in a container in an amount that provides a quantity sufficient for administration of at least one dose of a multi-dose regimen. Therefore, and viewed from a different perspective, the volume of ready-to-administer acetylcysteine will be sufficient to allow for administration of more than a single dose of a multi-dose regimen. Therefore, suitable quantities in a single container will be between 100 and 200 mL, or between 150 and 250 mL, or between 200 and 300 mL, or between 250 and 500 mL, or between 300 and 600 mL, or even higher. For example, the volume of ready-to-administer acetylcysteine in a single container may be 50 mL, 100 mL, 150 mL, 200 mL, 250 mL, 300 mL, or 500 mL, or even higher. The acetylcysteine concentration in such containers will preferably be 25 mg/mL or 50 mg/mL (however, other concentrations as discussed above are also deemed appropriate).

In still further contemplated embodiments, acetylcysteine will be administered in a multi-dose regimen comprising a first (loading) dose, a second (maintenance) dose, and a third (maintenance dose), with the second and third doses typically delivering distinct quantities over distinct periods of administration. Exemplary doses and schedules of administration are depicted in Table 3 (pediatric use) and Table 4 (non-pediatric use). The values given in the different doses indicate the amount of acetylcysteine administered with the corresponding volume listed in parentheses. As can be readily seen form the Tables, the concentration of acetylcysteine is constant over all three doses, and the quantity of acetylcysteine over a given time can be readily using a predetermined rate of administration (which will typically be performed via a rate-controlled infusion pump). Moreover, and especially for subjects with normal o lower body weight, it should be recognized that the overall fluid load is significantly lower as compared to administration of the same quantity of acetylcysteine when diluted from a concentrate.

TABLE 3

| Body Weight | Concentration | Bag 1 (Loading Dose) infused over 1 hour | Bag 2 (Second Dose) infused over 4 hours | Bag 3 (Third Dose) infused over 16 hours |
|---|---|---|---|---|
| 5 kg | 50 mg/mL | 750 mg (15 mL) | 250 mg (5 mL) | 500 mg (10 mL) |
| 10 kg | 50 mg/mL | 1,500 mg (30 mL) | 500 mg (10 mL) | 1,000 mg (20 mL) |
| 15 kg | 50 mg/mL | 2,250 mg (45 mL) | 750 mg (15 mL) | 1,500 mg (30 mL) |
| 20 kg | 50 mg/mL | 3,000 mg (60 mL) | 1,000 mg (20 mL) | 2,000 mg (40 mL) |

TABLE 4

| Body Weight | Concentration | Bag 1 (Loading Dose) infused over 1 hour | Bag 2 (Second Dose) infused over 4 hours | Bag 3 (Third Dose) infused over 16 hours |
|---|---|---|---|---|
| 21 kg | 25 mg/mL | 3,150 mg (126 mL) | 1,050 mg (42 mL) | 2,100 mg (84 mL) |
| 30 kg | 25 mg/mL | 4,500 mg (180 mL) | 1,500 mg (60 mL) | 3,000 mg (120 mL) |
| 40 kg | 25 mg/mL | 6,000 mg (240 mL) | 2,000 mg (80 mL) | 4,000 mg (160 mL) |
| 41 kg | 50 mg/mL | 6,150 mg (123 mL) | 2,050 mg (41 mL) | 4,100 mg (82 mL) |
| 50 kg | 50 mg/mL | 7,500 mg (150 mL) | 2,500 mg (50 mL) | 5,000 mg (100 mL) |
| 60 kg | 50 mg/mL | 9,000 mg (180 mL) | 3,000 mg (60 mL) | 6,000 mg (120 mL) |
| 70 kg | 50 mg/mL | 10,500 mg (210 mL) | 3,500 mg (70 mL) | 7,000 mg (140 mL) |
| 80 kg | 50 mg/mL | 12,000 mg (240 mL) | 4,000 mg (80 mL) | 8,000 mg (160 mL) |
| 90 kg | 50 mg/mL | 13,500 mg (270 mL) | 4,500 mg (90 mL) | 9,000 mg (180 mL) |
| ≥100 kg | 50 mg/mL | 15,000 mg (300 mL) | 5,000 mg (100 mL) | 10,000 mg (200 mL) |

EXAMPLES

The following examples are intended as representative embodiments of the inventive subject matter and should not be construed as limiting the scope of the invention.

Storage stability of acetylcysteine was evaluated at pH 6.0, 6.5, 7.0, 7.5 and 8.0. To that end, batches were manufactured in glass containers, and nitrogen sparging was performed on every step to ensure low levels of oxygen. All solutions were dispensed in polypropylene bags and were packaged (vacuum-sealed) in a secondary aluminum overwrap containing a non-contact oxygen scavenger. Samples were stored at 80° C. for up to 3 weeks. Tables 5-9 show exemplary results. As can be readily seen form the data, acetylcysteine in the tested formulations had desirable stability over a pH range of 6.0 to 7.5. Such observation was unexpected at the very low tested concentrations for acetylcysteine, particularly in the absence of buffer, other stabilizing agents, and antioxidants. However, acetylcysteine degradation was relatively higher at pH 8.0. Therefore, further evaluations were performed at pH 7.0.

TABLE 5

Lot # 14003-1
Stability data for 25 mg/mL Acetylcysteine at pH 6.0 (80° C.)

| Time point | | Initial | 1 Day | 4 Day | 1 Week | 2 Week | 3 Week |
|---|---|---|---|---|---|---|---|
| Appearance | | CCS | CCS | CCS | CCS | CCS | CCS |
| pH | | 6.81 | 6.56 | 6.40 | 6.52 | 6.29 | 6.23 |
| Dissolved Oxygen (ppm) | | 1.34 | 1.03 | 0.96 | 0.97 | 0.97 | 0.98 |
| Osmolality (mOsm/kg) | | 295 | 298 | 302 | 300 | 300 | 300 |
| Assay (%) | | 98.6 | 100.5 | 94.4 | 96.0 | 95.4 | 95.5 |
| Related substance (%) | RC-A | NR | NR | NR | NR | NR | NR |
| | RC-B | 0.24 | 0.56 | 0.90 | 1.21 | 1.75 | 2.40 |
| | RC-C | 0.45 | 0.59 | 1.48 | 0.81 | 0.86 | 1.47 |
| | RC-D | 0.27 | 0.22 | 0.15 | 0.13 | 0.10 | 0.09 |
| | Unknown (RRT) | NR | 0.06 (0.94) NR (1.06) | NR (0.30) 0.07 (0.41) NR (0.50) 0.19 (0.94) NR (1.06) NR (1.21) NR (1.38) NR (1.54) NR (1.60) | NR (0.30) NR (0.50) 0.31 (0.94) NR (1.06) 0.06 (1.21) NR (1.38) NR (1.54) NR (1.60) | 0.14 (0.30) 0.10 (0.50) 0.61 (0.94) NR (1.06) 0.16 (1.21) 0.05 (1.38) 0.05 (1.54) NR (1.60) | 0.31 (0.30) NR (0.46) 0.16 (0.50) 0.99 (0.94) NR (1.06) 0.33 (1.21) NR (1.35) 0.07 (1.38) NR (1.44) 0.09 (1.54) 0.08 (1.60) |
| Total Impurity (%) | | 0.95 | 1.43 | 2.78 | 2.53 | 3.82 | 6.02 |

TABLE 6

Lot # 14003-2
Stability data for 25 mg/mL Acetylcysteine at pH 6.5 (80° C.)

| Time point | | Initial | 1 Day | 4 Day | 1 Week | 2 Week | 3 Week |
|---|---|---|---|---|---|---|---|
| Appearance | | CCS | CCS | CCS | CCS | CCS | CCS |
| pH | | 6.94 | 6.75 | 6.60 | 6.52 | 6.46 | 6.39 |
| Dissolved Oxygen (ppm) | | 1.09 | 0.90 | 1.01 | 0.86 | 0.94 | 0.90 |
| Osmolality (mOsm/kg) | | 294 | 295 | 300 | 299 | 298 | 300 |
| Assay (%) | | 99.3 | 101.1 | 96.1 | 97.1 | 95.6 | 94.9 |
| Related substance (%) | RC-A | NR | NR | NR | NR | NR | NR |
| | RC-B | 0.22 | 0.44 | 0.89 | 1.16 | 1.73 | 2.28 |
| | RC-C | 0.34 | 0.43 | 0.52 | 0.47 | 0.78 | 1.09 |
| | RC-D | 0.22 | 0.18 | 0.10 | 0.09 | 0.07 | 0.07 |
| | Unknown (RRT) | NR | NR (0.94) NR (1.06) | NR (0.30) NR (0.50) 0.20 (0.94) NR (1.06) NR (1.21) NR (1.54) NR (1.60) | 0.05 (0.30) NR (0.50) 0.34 (0.94) NR (1.06) 0.07 (1.21) NR (1.38) NR (1.54) 0.06 (1.60) | 0.14 (0.30) 0.09 (0.50) 0.65 (0.94) NR (1.06) 0.20 (1.21) NR (1.38) 0.06 (1.54) 0.06 (1.60) | 0.30 (0.30) 0.15 (0.50) NR (0.80) 1.00 (0.94) NR (1.06) 0.37 (1.21) NR (1.35) 0.07 (1.38) NR (1.44) 0.13 (1.54) NR (1.57) 0.09 (1.60) |
| Total Impurity (%) | | 0.77 | 1.04 | 1.71 | 2.19 | 3.79 | 5.57 |

TABLE 7

Lot # 14003-3
Stability data for 25 mg/mL Acetylcysteine at pH7.0 (80° C.)

| Time point | Initial | 1 Day | 4 Day | 1 Week | 2 Week | 3 Week |
|---|---|---|---|---|---|---|
| Appearance | CCS | CCS | CCS | CCS | CCS | CCS |
| pH | 7.16 | 7.03 | 7.01 | 6.87 | 6.80 | 6.81 |
| Dissolved Oxygen (ppm) | 0.95 | 0.94 | 1.00 | 0.99 | 0.86 | 0.99 |

TABLE 7-continued

Lot # 14003-3
Stability data for 25 mg/mL Acetylcysteine at pH7.0 (80° C.)

| Time point | | Initial | 1 Day | 4 Day | 1 Week | 2 Week | 3 Week |
|---|---|---|---|---|---|---|---|
| Osmolality (mOsm/kg) | | 297 | 297 | 300 | 299 | 301 | 298 |
| Assay (%) | | 99.5 | 101.1 | 95.3 | 97.3 | 95.8 | 96.5 |
| Related substance (%) | RC-A | NR | NR | NR | NR | NR | NR |
| | RC-B | 0.19 | 0.42 | 0.69 | 1.01 | 1.45 | 1.91 |
| | RC-C | 0.41 | 0.42 | 0.52 | 0.56 | 1.04 | 1.18 |
| | RC-D | 0.16 | 0.10 | NR | NR | NR | NR |
| | Unknown (RRT) | NR | NR (0.94) | NR (0.30) | NR (0.30) | 0.12 (0.30) | 0.27 (0.30) |
| | | | NR (1.06) | NR (0.50) | NR (0.50) | 0.08 (0.50) | 0.15 (0.50) |
| | | | | 0.21 (0.94) | 0.33 (0.94) | NR (0.80) | NR (0.71) |
| | | | | NR (1.06) | NR (1.06) | 0.66 (0.94) | NR (0.80) |
| | | | | NR (1.21) | 0.07 (1.21) | NR (1.06) | 1.07 (0.94) |
| | | | | NR (1.38) | NR (1.38) | 0.21 (1.21) | NR (1.06) |
| | | | | NR (1.54) | NR (1.54) | NR (1.38) | 0.43 (1.21) |
| | | | | NR (1.60) | NR (1.60) | 0.10 (1.54) | 0.06 (1.35) |
| | | | | | | 0.10 (1.60) | 0.06 (1.38) |
| | | | | | | | NR (1.44) |
| | | | | | | | 0.19 (1.54) |
| | | | | | | | 0.16 (1.60) |
| Total Impurity (%) | | 0.77 | 0.94 | 1.42 | 1.98 | 3.76 | 5.47 |

TABLE 8

Lot # 14003-4
Stability data for 25 mg/mL Acetylcysteine at pH 7.5 (80° C.)

| Time point | | Initial | 1 Day | 4 Day | 1 Week | 2 Week | 3 Week |
|---|---|---|---|---|---|---|---|
| Appearance | | CCS | CCS | CCS | CCS | CCS | CCS |
| pH | | 7.65 | 7.49 | 7.49 | 7.37 | 7.32 | 7.30 |
| Dissolved Oxygen (ppm) | | 1.05 | 0.85 | 1.00 | 0.92 | 0.82 | 1.00 |
| Osmolality (mOsm/kg) | | 296 | 296 | 300 | 300 | 303 | 296 |
| Assay (%) | | 99.7 | 100.9 | 96.3 | 97.4 | 95.4 | 94.3 |
| Related substance (%) | RC-A | NR | NR | NR | NR | NR | NR |
| | RC-B | 0.11 | 0.39 | 0.65 | 0.92 | 1.21 | 1.46 |
| | RC-C | 0.64 | 0.70 | 0.92 | 0.54 | 1.15 | 1.61 |
| | RC-D | 0.11 | NR | NR | NR | NR | NR |
| | Unknown (RRT) | NR | NR (0.94) | NR (0.30) | NR (0.30) | 0.11 (0.30) | 0.24 (0.30) |
| | | | NR (1.06) | NR (0.50) | NR (0.50) | 0.09 (0.50) | 0.15 (0.50) |
| | | | | 0.22 (0.94) | 0.38 (0.94) | NR (0.80) | NR (0.71) |
| | | | | NR (1.06) | NR (1.06) | 0.76 (0.94) | 0.05 (0.80) |
| | | | | NR (1.21) | 0.10 (1.21) | NR (1.06) | 1.21 (0.94) |
| | | | | NR (1.38) | NR (1.38) | 0.29 (1.21) | NR (1.06) |
| | | | | 0.05 (1.54) | 0.11 (1.54) | NR (1.34) | 0.55 (1.21) |
| | | | | 0.05 (1.60) | 0.10 (1.60) | 0.27 (1.54) | 0.12 (1.35) |
| | | | | | | 0.24 (1.60) | NR (1.38) |
| | | | | | | | 0.42 (1.54) |
| | | | | | | | 0.37 (1.60) |
| Total Impurity (%) | | 0.86 | 1.09 | 1.89 | 2.15 | 4.13 | 6.18 |

TABLE 9

Lot # 14003-5
Stability data for 25 mg/mL Acetylcysteine at pH 8.0 (80° C.)

| Time point | Initial | 1 Day | 4 Day | 1 Week | 2 Week | 3 Week |
|---|---|---|---|---|---|---|
| Appearance | CCS | CCS | CCS | CCS | CCS | CCS |
| pH | 8.05 | 7.95 | 7.92 | 7.89 | 7.83 | 7.84 |
| Dissolved Oxygen (ppm) | 1.02 | 0.90 | 0.93 | 0.88 | 0.93 | 0.88 |

TABLE 9-continued

Lot # 14003-5
Stability data for 25 mg/mL Acetylcysteine at pH 8.0 (80° C.)

| Time point | | Initial | 1 Day | 4 Day | 1 Week | 2 Week | 3 Week |
|---|---|---|---|---|---|---|---|
| Osmolality (mOsm/kg) | | 298 | 296 | 297 | 300 | 301 | 293 |
| Assay (%) | | 99.9 | 100.5 | 91.4 | 96.4 | 92.4 | 94.1 |
| Related substance (%) | RC-A | NR | NR | NR | NR | NR | NR |
| | RC-B | 0.10 | 0.49 | 0.56 | 0.87 | 0.97 | 1.09 |
| | RC-C | 0.52 | 0.69 | 4.81 | 0.79 | 2.72 | 1.55 |
| | RC-D | 0.06 | NR | NR | NR | NR | NR |
| | Unknown (RRT) | NR | 0.08 (0.94) | NR (0.30) | NR (0.30) | 0.09 (0.30) | 0.18 (0.30) |
| | | | NR (1.06) | 0.26 (0.41) | 0.05 (0.50) | 0.11 (0.41) | NR (0.33) |
| | | | | NR (0.50) | 0.42 (0.94) | 0.12 (0.50) | NR (0.46) |
| | | | | 0.25 (0.94) | NR (1.06) | NR (0.71) | 0.19 (0.50) |
| | | | | NR (1.06) | 0.12 (1.21) | NR (0.80) | 0.06 (0.71) |
| | | | | 0.05 (1.21) | 0.24 (1.54) | 0.92 (0.94) | 0.07 (0.80) |
| | | | | 0.11 (1.54) | 0.24 (1.60) | NR (1.06) | 1.51 (0.94) |
| | | | | 0.11 (1.60) | | 0.36 (1.21) | NR (1.06) |
| | | | | | | 0.10 (1.34) | 0.69 (1.21) |
| | | | | | | 0.63 (1.54) | NR (1.47) |
| | | | | | | 0.59 (1.60) | 1.09 (1.54) |
| | | | | | | | 0.92 (1.60) |
| | | | | | | | NR (1.67) |
| Total Impurity (%) | | 0.68 | 1.27 | 6.15 | 2.73 | 6.6 | 7.35 |

The inventors then investigated the effect of a metal chelator in acetylcysteine formulations. To that end, samples were prepared at pH 7.0 that included edetate disodium dihydrate (EDTA) at concentrations of either 0 mcg/mL (control), 10 mcg/mL, 20 mcg/mL, 30 mcg/mL, 40 mcg/mL, and 60 mcg/mL. Once again, the samples were manufactured in glass containers, and nitrogen sparging was performed on every step to ensure low levels of oxygen. Solutions were dispensed in polypropylene bags and were packaged (vacuum-sealed) in a secondary aluminum overwrap containing a non-contact oxygen scavenger. The samples were stored at either 60° C. for up to 2 weeks or at 80° C. for up to 1 week as indicated, and exemplary results are shown in Tables 10-15. While the effects did not reveal a trend or change in stability, it should be noted that the chelator also did not adversely affect stability at the tested low concentrations. In that regard, it is contemplated that where manufacture is modified to include steel containers, metal leakage and associated metal-catalyzed degradation may occur unless a chelator is employed.

TABLE 10

Stability data for 25 mg/mL Acetylcysteine at pH 7.0 containing 0 mcg/mL EDTA (control)

Lot #13991-1

| | | | 60° C. | | | 80° C. | | |
|---|---|---|---|---|---|---|---|---|
| Time point | | Initial | 4 Day | 1 Week | 2 Week | 1 Day | 4 Day | 1 Week |
| Appearance | | CCS | CCS | CCS | CCS | CCS | CCS | CCS |
| pH | | 7.18 | 7.01 | 7.04 | 6.96 | 7.01 | 6.87 | 6.85 |
| Dissolved Oxygen (ppm) | | 1.01 | 1.05 | 0.96 | 1.07 | 0.96 | 0.96 | 0.90 |
| Osmolality (mOsm/kg) | | 298 | 296 | 296 | 296 | 295 | 300 | 297 |
| Assay (%) | | 98.5 | 97.9 | 99.1 | 100.4 | 100.2 | 95.7 | 98.2 |
| Related substance (%) | RC-A | NR | NR | NR | NR | NR | NR | NR |
| | RC-B | 0.18 | 0.23 | 0.37 | 0.56 | 0.42 | 0.72 | 1.15 |
| | RC-C | 0.32 | 0.33 | 0.31 | 0.34 | 0.56 | 0.53 | 0.48 |
| | RC-D | 0.17 | 0.12 | 0.10 | 0.07 | 0.11 | 0.05 | NR |
| | Unknown (RRT) | NR | NR (0.94) | NR (0.94) | NR (0.50) | NR (0.94) | NR (0.30) | 0.05 (0.30) |
| | | | | | 0.07 (0.94) | NR (1.06) | NR (0.50) | NR (0.50) |
| | | | | | NR (1.06) | | 0.21 (0.94) | 0.38 (0.94) |
| | | | | | | | NR (1.06) | NR (1.06) |
| | | | | | | | NR (1.21) | 0.10 (1.21) |
| | | | | | | | NR (1.60) | NR (1.38) |
| | | | | | | | | 0.05 (1.54) |
| | | | | | | | | 0.06 (1.60) |
| Total Impurity (%) | | 0.67 | 0.67 | 0.78 | 1.04 | 1.09 | 1.52 | 2.27 |

TABLE 11

Stability data for 25 mg/mL Acetylcysteine at pH 7.0 containing 10 mcg/mL EDTA

Lot #13991-2

| | | | 60° C. | | | 80° C. | | |
|---|---|---|---|---|---|---|---|---|
| Time point | | Initial | 4 Day | 1 Week | 2 Week | 1 Day | 4 Day | 1 Week |
| Appearance | | CCS | CCS | CCS | CCS | CCS | CCS | CCS |
| pH | | 7.28 | 7.21 | 7.25 | 7.22 | 7.22 | 7.08 | 7.23 |
| Dissolved Oxygen (ppm) | | 0.94 | 0.95 | 0.91 | 1.04 | 0.92 | 0.97 | 0.96 |
| Osmolality (mOsm/kg) | | 293 | 294 | 295 | 293 | 293 | 298 | 294 |
| Assay (%) | | 98.2 | 96.8 | 98.7 | 100.3 | 99.1 | 94.6 | 97.2 |
| Related substance (%) | RC-A | NR | NR | NR | NR | NR | NR | NR |
| | RC-B | 0.18 | 0.26 | 0.36 | 0.48 | 0.40 | 0.80 | 1.03 |
| | RC-C | 0.20 | 0.39 | 0.32 | 0.29 | 0.39 | 0.43 | 0.44 |
| | RC-D | 0.14 | 0.08 | 0.06 | 0.07 | 0.07 | NR | NR |
| | Unknown (RRT) | NR | NR (0.94) | NR (0.94) | NR (0.50) | NR (0.94) | NR (0.30) | 0.05 (0.30) |
| | | | NR (1.06) | | 0.08 (0.94) | NR (1.06) | NR (0.50) | NR (0.50) |
| | | | | | NR (1.06) | | 0.22 (0.94) | 0.40 (0.94) |
| | | | | | NR (1.21) | | NR (1.06) | NR (1.06) |
| | | | | | | | NR (1.21) | 0.11 (1.21) |
| | | | | | | | NR (1.38) | NR (1.38) |
| | | | | | | | NR (1.44) | 0.07 (1.54) |
| | | | | | | | NR (1.54) | 0.07 (1.60) |
| | | | | | | | NR (1.60) | |
| Total Impurity (%) | | 0.53 | 0.74 | 0.74 | 0.86 | 1.09 | 1.52 | 2.27 |

TABLE 12

Stability data for 25 mg/mL Acetylcysteine at pH 7.0 containing 20 mcg/mL EDTA

Lot #13991-2

| | | | 60° C. | | | 80° C. | | |
|---|---|---|---|---|---|---|---|---|
| Time point | | Initial | 4 Day | 1 Week | 2 Week | 1 Day | 4 Day | 1 Week |
| Appearance | | CCS | CCS | CCS | CCS | CCS | CCS | CCS |
| pH | | 7.24 | 7.10 | 7.20 | 7.08 | 7.17 | 6.96 | 7.01 |
| Dissolved Oxygen (ppm) | | 0.90 | 1.02 | 0.98 | 1.15 | 0.87 | 0.88 | 0.88 |
| Osmolality (mOsm/kg) | | 298 | 301 | 297 | 301 | 299 | 297 | 300 |
| Assay (%) | | 99.4 | 98.2 | 100.2 | 101.6 | 100.8 | 97.2 | 97.8 |
| Related substance (%) | RC-A | NR | NR | NR | NR | NR | NR | NR |
| | RC-B | 0.18 | 0.27 | 0.38 | 0.54 | 0.44 | 0.86 | 1.07 |
| | RC-C | 0.40 | 0.40 | 0.38 | 0.38 | 0.50 | 0.55 | 0.52 |
| | RC-D | 0.16 | 0.10 | 0.08 | 0.06 | 0.09 | NR | NR |
| | Unknown (RRT) | NR | NR (0.94) | NR (0.94) | NR (0.50) | NR (0.94) | NR (0.30) | 0.06 (0.30) |
| | | | | | 0.08 (0.94) | NR (1.06) | NR (0.50) | 0.05 (0.50) |
| | | | | | NR (1.06) | | 0.23 (0.94) | 0.42 (0.94) |
| | | | | | NR (1.21) | | NR (1.06) | NR (1.06) |
| | | | | | | | 0.05 (1.21) | 0.11 (1.21) |
| | | | | | | | NR (1.38) | NR (1.38) |
| | | | | | | | NR (1.44) | 0.06 (1.54) |
| | | | | | | | NR (1.54) | 0.06 (1.60) |
| | | | | | | | NR (1.60) | |
| Total Impurity (%) | | 0.74 | 0.76 | 0.84 | 1.06 | 1.04 | 1.69 | 2.36 |

TABLE 13

Stability data for 25 mg/mL Acetylcysteine at pH 7.0 containing 30 mcg/mL EDTA

Lot# 13991-4

| | | | 60° C. | | | 80° C. | | |
|---|---|---|---|---|---|---|---|---|
| Time point | | Initial | 4 Day | 1 Week | 2 Week | 1 Day | 4 Day | 1 Week |
| Appearance | | CCS | CCS | CCS | CCS | CCS | CCS | CCS |
| pH | | 7.20 | 7.17 | 7.22 | 7.09 | 7.12 | 6.98 | 7.03 |
| Dissolved Oxygen (ppm) | | 1.08 | 0.99 | 0.85 | 1.17 | 0.87 | 0.93 | 0.96 |
| Osmolality (mOsm/kg) | | 298 | 299 | 301 | 290 | 296 | 296 | 296 |
| Assay (%) | | 99.3 | 96.7 | 100.4 | 101.9 | 101.2 | 97.4 | 98.4 |
| Related substance (%) | RC-A | NR | NR | NR | NR | NR | NR | NR |
| | RC-B | 0.17 | 0.27 | 0.37 | 0.56 | 0.40 | 0.86 | 1.11 |
| | RC-C | 0.20 | 0.14 | 0.23 | 0.19 | 0.25 | 0.26 | 0.32 |
| | RC-D | 0.16 | 0.10 | 0.08 | 0.06 | 0.09 | NR | NR |
| | Unknown (RRT) | NR | NR (0.94) | NR (0.94) | NR (0.50) 0.07 (0.94) NR (1.06) | NR (0.94) NR (1.06) | NR (0.30) NR (0.50) 0.23 (0.94) NR (1.06) NR (1.21) NR (1.38) NR (1.44) NR (1.54) NR (1.60) | 0.06 (0.30) NR (0.50) 0.41 (0.94) NR (1.06) 0.11 (1.21) NR (1.38) 0.06 (1.54) 0.06 (1.60) |
| Total Impurity (%) | | 0.53 | 0.51 | 0.69 | 0.88 | 0.74 | 1.35 | 2.12 |

TABLE 14

Stability data for 25 mg/mL Acetylcysteine at pH 7.0 containing 40 mcg/mL EDTA

Lot #13991-5

| | | | 60° C. | | | 80° C. | | |
|---|---|---|---|---|---|---|---|---|
| Time point | | Initial | 4 Day | 1 Week | 2 Week | 1 Day | 4 Day | 1 Week |
| Appearance | | CCS | CCS | CCS | CCS | CCS | CCS | CCS |
| pH | | 7.15 | 7.10 | 7.16 | 7.00 | 7.09 | 6.93 | 7.01 |
| Dissolved Oxygen (ppm) | | 0.98 | 1.03 | 0.98 | 1.00 | 1.00 | 0.85 | 0.93 |
| Osmolality (mOsm/kg) | | 301 | 300 | 296 | 298 | 298 | 300 | 299 |
| Assay (%) | | 99.4 | 98.1 | 99.8 | 102.0 | 100.9 | 95.7 | 97.9 |
| Related substance (%) | RC-A | NR | NR | NR | NR | NR | NR | NR |
| | RC-B | 0.19 | 0.29 | 0.38 | 0.58 | 0.42 | 0.84 | 1.07 |
| | RC-C | 0.22 | 0.23 | 0.21 | 0.18 | 0.35 | 0.32 | 0.38 |
| | RC-D | 0.16 | 0.11 | 0.09 | 0.07 | 0.10 | NR | NR |
| | Unknown (RRT) | NR | NR (0.94) | NR (0.94) | NR (0.50) 0.07 (0.94) NR (1.06) NR (1.21) | NR (0.94) NR (1.06) | NR (0.30) NR (0.50) 0.22 (0.94) NR (1.06) NR (1.21) NR (1.38) NR (1.54) NR (1.60) | 0.06 (0.30) NR (0.50) 0.39 (0.94) NR (1.06) 0.10 (1.21) NR (1.38) 0.05 (1.54) NR (1.60) |
| Total Impurity (%) | | 0.57 | 0.63 | 0.68 | 0.90 | 0.88 | 1.38 | 2.05 |

TABLE 15

Stability data for 25 mg/mL Acetylcysteine at pH 7.0 containing 60 mcg/mL EDTA

Lot #13991-6

| | | 60° C. | | | 80° C. | | |
|---|---|---|---|---|---|---|---|
| Time point | Initial | 4 Day | 1 Week | 2 Week | 1 Day | 4 Day | 1 Week |
| Appearance | CCS | CCS | CCS | CCS | CCS | CCS | CCS |
| pH | 7.17 | 7.10 | 7.22 | 7.08 | 7.09 | 6.98 | 7.06 |

TABLE 15-continued

Stability data for 25 mg/mL Acetylcysteine at pH 7.0 containing 60 mcg/mL EDTA

Lot #13991-6

| | | | 60° C. | | | 80° C. | | |
|---|---|---|---|---|---|---|---|---|
| Time point | | Initial | 4 Day | 1 Week | 2 Week | 1 Day | 4 Day | 1 Week |
| Dissolved Oxygen (ppm) | | 1.05 | 1.07 | 0.92 | 0.95 | 1.01 | 0.89 | 0.91 |
| Osmolality (mOsm/kg) | | 296 | 302 | 298 | 296 | 297 | 301 | 302 |
| Assay (%) | | 99.4 | 98.0 | 99.9 | 102.2 | 100.6 | 95.1 | 96.5 |
| Related substance (%) | RC-A | NR | NR | NR | NR | NR | NR | NR |
| | RC-B | 0.18 | 0.36 | 0.37 | 0.58 | 0.41 | 0.85 | 1.08 |
| | RC-C | 0.26 | 0.29 | 0.29 | 0.34 | 0.44 | 0.50 | 0.68 |
| | RC-D | 0.16 | 0.10 | 0.08 | 0.06 | 0.10 | NR | NR |
| | Unknown (RRT) | NR | NR (0.94) | NR (0.94) | 0.08 (0.94) NR (1.06) NR (1.21) | NR (0.94) NR (1.06) | NR (0.30) NR (0.50) 0.24 (0.94) NR (1.06) NR (1.21) NR (1.38) NR (1.54) NR (1.60) | 0.06 (0.30) NR (0.50) 0.42 (0.94) 0.11 (1.21) NR (1.38) 0.06 (1.54) 0.06 (1.60) |
| Total Impurity (%) | | 0.60 | 0.75 | 0.74 | 1.06 | 0.94 | 1.60 | 2.48 |

In still further experiments, the inventors sought to determine the feasibility of terminal sterilization (here: autoclaving) via an air overpressure (AOP) cycle at 121° C. for either 15-mins or 30-mins exposure time (ET). Acetylcysteine solutions were prepared at pH 7.0 with or without EDTA (as indicated in above). Samples were manufactured in glass containers, and nitrogen sparging was performed on every step to ensure low levels of oxygen. Solutions were dispensed in polypropylene bags. Accordingly, bags were either autoclaved before (Table 16) or after packaging (Table 17), unless otherwise indicated. Bags handled following the former sterilization process were then cooled after autoclaving and packaged (vacuum-sealed) in a secondary aluminum overwrap containing a non-contact oxygen scavenger. Bags following the later sterilization process were packaged (vacuum-sealed) initially in secondary aluminum overwrap containing an autoclavable non-contact oxygen scavenger and held at room temperature for 2 days prior to autoclaving. No further packaging steps were performed after autoclaving. In this context, it should be noted that the overwrap need not necessarily be metallized or otherwise light impermeable.

Bags that were not autoclaved were packaged similarly to previous studies, where bags were encased (vacuum-sealed) in a secondary aluminum overwrap containing a non-contact oxygen scavenger. As can be seen form the results in Tables 16 and 17, the impurity levels in autoclaved acetylcysteine solutions were higher as compared to not-autoclaved (aseptically filled) batches (Table 16). Notably, it appeared that the sterilization process in which the bags were packaged prior to autoclaving (Table 17) resulted in lower impurity levels as compared to the sterilization process wherein bare bags were autoclaved (Table 16). However, both sterilization techniques yielded higher impurity levels as compared to aseptic filling (preferably performed using sterile filtration).

TABLE 16

25 mg/mL Acetylcysteine at pH 7.0 containing either 20 mcg/mL or 60 mcg/mL
EDTA and either autoclaved (before packaging) or not autoclaved

| | | Amount of EDTA in formulation | | | | | |
|---|---|---|---|---|---|---|---|
| | | 20 mcg/mL EDTA (Lot # 13992-1) | | | 60 mcg/mL EDTA (Lot # 13992-4) | | |
| Condition | | Not autoclaved | 15 mins ET | 30 mins ET | Not autoclaved | 15 mins ET | 30 mins ET |
| Appearance | | CCS | CCS | CCS | CCS | CCS | CCS |
| pH | | 7.22 | 6.98 | 7.06 | 7.25 | 7.06 | 7.06 |
| Dissolved Oxygen (ppm) | | 0.92 | 1.18 | 1.09 | 0.95 | 1.03 | 1.04 |
| Osmolality (mOsm/kg) | | 296 | 296 | 296 | 349* | 347* | 347* |
| Assay (%) | | 102.4 | 101.9 | 99.4 | 103.0 | 99.0 | 99.1 |
| Related substance (%) | RC-A | NR | NR | NR | NR | NR | NR |
| | RC-B | 0.18 | 0.35 | 0.37 | 0.20 | 0.33 | 0.40 |
| | RC-C | 0.80 | 1.95 | 2.00 | 0.34 | 1.36 | 1.46 |
| | RC-D | 0.15 | 0.12 | 0.13 | 0.16 | 0.12 | 0.12 |
| | Unknown (RRT) | NR | 0.05 (0.94) 0.06 (1.06) 0.15 (1.12) | 0.06 (0.94) 0.08 (1.06) 0.15 (1.12) | NR (0.33) | NR (0.94) 0.13 (1.12) NR (1.21) | 0.08 (0.94) NR (1.06) 0.23 (1.12) |

TABLE 16-continued 25 mg/mL Acetylcysteine at pH 7.0 containing either 20 mcg/mL or 60 mcg/mL
EDTA and either autoclaved (before packaging) or not autoclaved

| | Amount of EDTA in formulation | | | | | |
|---|---|---|---|---|---|---|
| | 20 mcg/mL EDTA (Lot # 13992-1) | | | 60 mcg/mL EDTA (Lot # 13992-4) | | |
| Condition | Not autoclaved | 15 mins ET | 30 mins ET | Not autoclaved | 15 mins ET | 30 mins ET |
| | | 0.05 (1.21) | 0.06 (1.21) | | NR (1.54) | 0.08 (1.21) |
| | | NR (1.54) | NR (1.54) | | | 0.05 (1.54) |
| | | | NR (1.60) | | | NR (1.60) |
| Total Impurity (%) | 1.13 | 2.73 | 2.86 | 0.70 | 1.95 | 2.42 |

TABLE 17

25 mg/mL Acetylcysteine at pH 7.0 containing varying levels of EDTA
and autoclaved after packaging with ATCO HV300M oxygen scavenger

| | | Lot# 14172 | | | | | |
|---|---|---|---|---|---|---|---|
| | | 0 mcg/mL EDTA | 10 mcg/mL EDTA | 20 mcg/mL EDTA | 30 mcg/mL EDTA | 40 mcg/mL EDTA | 60 mcg/mL EDTA |
| Appearance | | CCS | CCS | CCS | CCS | CCS | CCS |
| pH | | 6.94 | 7.06 | 7.01 | 7.03 | 7.01 | 7.03 |
| Dissolved Oxygen (ppm) | | 1.14 | 1.28 | 1.21 | 1.19 | 1.08 | 1.19 |
| Osmolality (mOsm/kg) | | 295 | 288 | 304 | 298 | 295 | 302 |
| Assay (%) | | 100.4 | 99.2 | 97.7 | 99.1 | 99.9 | 100.1 |
| Related | RC-A | NR | NR | NR | NR | NR | NR |
| substance | RC-B | 0.52 | 0.44 | 0.47 | 0.46 | 0.50 | 0.43 |
| (%) | RC-C | 0.53 | 0.42 | 0.47 | 0.30 | 0.47 | 0.50 |
| | RC-D | 0.14 | 0.09 | 0.11 | 0.11 | 0.12 | 0.12 |
| | Unknown (RRT) | 0.08 (0.94) | 0.09 (0.94) | 0.07 (0.94) | 0.07 (0.94) | 0.08 (0.94) | 0.09 (0.94) |
| | | 0.23 (1.06) | 0.24 (1.06) | 0.21 (1.06) | 0.21 (1.06) | 0.22 (1.06) | 0.24 (1.06) |
| | | 0.06 (1.21) | 0.06 (1.21) | 0.06 (1.21) | 0.05 (1.21) | 0.06 (1.21) | 0.07 (1.21) |
| | | NR (1.54) | NR (1.38) | NR (1.38) | NR (1.38) | NR (1.38) | NR (1.38) |
| | | NR (1.60) | NR (1.54) | NR (1.54) | NR (1.54) | NR (1.54) | NR (1.54) |
| | | | NR (1.60) | NR (1.60) | NR (1.60) | NR (1.60) | NR (1.60) |
| | | | | | | NR (1.64) | |
| Total Impurity (%) | | 1.55 | 1.33 | 1.40 | 1.21 | 1.46 | 1.44 |

Acetylcysteine and its impurities were determined by a reverse phase HPLC method. The method was modified version of an EP method for Acetylcysteine. The column used was Phenomenex Luna® 5 μm C18(2) 100 Å (column dimension 250×4.6 mm) and a gradient of 0.1% phosphoric acid in water and acetonitrile was used as a mobile phase for analysis. Quantitation of Acetylcysteine is accomplished by comparing corresponding peak areas from sample solution chromatogram to that from a Reference Standard (RS) solution of a known concentration. The diluent solution used comprise of EDTA dissolved in water (0.06 mg/mL) and pH adjusted to 7.0±0.1 with 0.1N sodium hydroxide. Water used to prepare the diluent was degassed to achieve a dissolved oxygen level below 1 ppm and the sample temperature was maintained at 5° C. to prevent the oxidation of Acetylcysteine during analysis.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of administering N-acetylcysteine to a subject in need thereof, comprising:
    providing a sterile and ready-to-administer composition comprising N-acetylcysteine containing N-acetylcysteine at a fixed concentration of between 1 and 50 mg/mL, wherein the ready-to-administer composition has a pH of between 6.0 and 7.5;
    infusing, without prior dilution, the ready-to-administer composition to a subject in need thereof in three distinct doses, wherein the fixed concentration of the N-acetylcysteine is the same in each of the three doses; and
    wherein the ready-to-administer composition contains, after storage over at least three weeks at 80° C., equal or less than 7% total impurities generated from degradation of the N-acetylcysteine.

2. The method of claim 1 wherein the fixed concentration is 25 mg/mL or 50 mg/mL.

3. The method of claim 1 wherein the ready-to-administer composition comprises a metal chelator and has a pH of between 7.0 and 7.5, and optionally further comprises an antioxidant and/or a tonicity agent.

4. The method of claim 1 wherein administration of a first dose and at least part of a second dose of the three doses is done from a single container containing the ready-to-administer composition.

5. The method of claim 1 wherein administration of each of the three doses is done from respective separate containers, each containing the ready-to-administer composition.

6. The method of claim 4 wherein the container has a volume of between 200 and 300 mL.

7. The method of claim 3 wherein the metal chelator is ethylenediamine tetraacetic acid and is present at a concentration of between 1 and 60 mcg/mL.

8. The method of claim 1 wherein a first of the three doses is administered over 1 hour, wherein a second of the three doses is administered over 4 hours, and wherein a third of the three doses is administered over 16 hours.

9. The method of claim 1 wherein administering the ready-to-administer composition is performed using an infusion pump.

10. The method of claim 1 wherein the tonicity agent is sodium chloride, dextrose, and/or mannitol, and wherein the composition is filter sterilized.

11. The method of claim 1 wherein the infusion is performed according to a schedule in which
    the fixed concentration is 50 mg/mL, and in which a first dose of 15 mL is administered over 1 hour, a second dose of 5 mL is administered over 4 hours, and a third dose of 10 mL is administered over 16 hours when the body weight of the subject is 5 kg; or
    the fixed concentration is 50 mg/mL, and in which a first dose of 30 mL is administered over 1 hour, a second dose of 10 mL is administered over 4 hours, and a third dose of 20 mL is administered over 16 hours when the body weight of the subject is 10 kg; or
    the fixed concentration is 50 mg/mL, and in which a first dose of 45 mL is administered over 1 hour, a second dose of 15 mL is administered over 4 hours, and a third dose of 30 mL is administered over 16 hours when the body weight of the subject is 15 kg; or
    the fixed concentration is 50 mg/mL, and in which a first dose of 60 mL is administered over 1 hour, a second dose of 20 mL is administered over 4 hours, and a third dose of 40 mL is administered over 16 hours when the body weight of the subject is 20 kg; or
    the fixed concentration is 25 mg/mL, and in which a first dose of 126 mL is administered over 1 hour, a second dose of 42 mL is administered over 4 hours, and a third dose of 84 mL is administered over 16 hours when the body weight of the subject is 21 kg; or
    the fixed concentration is 25 mg/mL, and in which a first dose of 180 mL is administered over 1 hour, a second dose of 60 mL is administered over 4 hours, and a third dose of 120 mL is administered over 16 hours when the body weight of the subject is 30 kg; or
    the fixed concentration is 25 mg/mL, and in which a first dose of 240 mL is administered over 1 hour, a second dose of 80 mL is administered over 4 hours, and a third dose of 160 mL is administered over 16 hours when the body weight of the subject is 40 kg; or
    the fixed concentration is 50 mg/mL, and in which a first dose of 123 mL is administered over 1 hour, a second dose of 41 mL is administered over 4 hours, and a third dose of 82 mL is administered over 16 hours when the body weight of the subject is 41 kg; or
    the fixed concentration is 50 mg/mL, and in which a first dose of 150 mL is administered over 1 hour, a second dose of 50 mL is administered over 4 hours, and a third dose of 100 mL is administered over 16 hours when the body weight of the subject is 50 kg; or
    the fixed concentration is 50 mg/mL, and in which a first dose of 180 mL is administered over 1 hour, a second dose of 60 mL is administered over 4 hours, and a third dose of 120 mL is administered over 16 hours when the body weight of the subject is 60 kg; or
    the fixed concentration is 50 mg/mL, and in which a first dose of 210 mL is administered over 1 hour, a second dose of 70 mL is administered over 4 hours, and a third dose of 140 mL is administered over 16 hours when the body weight of the subject is 70 kg; or
    the fixed concentration is 50 mg/mL, and in which a first dose of 240 mL is administered over 1 hour, a second dose of 80 mL is administered over 4 hours, and a third dose of 160 mL is administered over 16 hours when the body weight of the subject is 80 kg; or
    the fixed concentration is 50 mg/mL, and in which a first dose of 270 mL is administered over 1 hour, a second dose of 90 mL is administered over 4 hours, and a third dose of 180 mL is administered over 16 hours when the body weight of the subject is 90 kg; or the fixed concentration is 50 mg/mL, and in which a first dose of 300 mL is administered over 1 hour, a second dose of 100 mL is administered over 4 hours, and a third dose of 200 mL is administered over 16 hours when the body weight of the subject is 100 kg or heavier.

12. The method of claim 1 wherein the ready-to-administer composition contains, after storage over at least three weeks at 80° C., equal or less than 6% total impurities generated from degradation of the N-acetylcysteine.

* * * * *